United States Patent [19]

Case, Jr. et al.

[11] Patent Number: 4,859,830
[45] Date of Patent: Aug. 22, 1989

[54] METHOD OF DETERMINING THE WELDABILITY OF A PART

[75] Inventors: Allen W. Case, Jr., Amsterdam; Robert D. Lillquist, Schenectady; Robert E. Sundell, Clifton Park, all of N.Y.

[73] Assignee: General Electric Company, Schenectady, N.Y.

[21] Appl. No.: 104,609

[22] Filed: Oct. 5, 1987

[51] Int. Cl.$^4$ ................................................. B23K 9/23
[52] U.S. Cl. .......................... 219/130.01; 219/130.21; 219/137 PS
[58] Field of Search ....................... 219/130.01, 130.21, 219/137 PS

[56] References Cited

U.S. PATENT DOCUMENTS

| | | | |
|---|---|---|---|
| 3,158,734 | 11/1964 | Manz | 219/131 |
| 3,632,960 | 1/1972 | Friedrich et al. | 219/131 |
| 4,435,631 | 3/1984 | Drouet et al. | 219/124.02 |
| 4,454,408 | 6/1984 | Kajiwara et al. | 219/124.34 |
| 4,595,820 | 6/1986 | Richardson | 219/137 |
| 4,613,743 | 9/1986 | Nied et al. | 219/130.21 |
| 4,711,986 | 12/1987 | Lillquist et al. | 219/130.01 |

OTHER PUBLICATIONS

Cary, *Modern Welding Technology*, 1979, p. 401.
Masubuchi, K., et al., "Improvement of Reliability of Welding by In-Process Sensing and Control", Massachusetts Inst. of Technology, American Society of Metals, pp. 667–695, 1982.
Zacksenhouse, M., "Weld Pool Impedance Identification for Size Measurement and Control", Massachusetts Institute of Technology, Proceedings of the Winter Annuals Meeting of the American Society Mechanical Engineers, pp. 77–88, Nov. 1982.
Mills, K. C. et al., "The Surface Tensions of 304 and 316 Type Stainless Steels and Their Effect on Weld Penetration," in Proc. Centenary Conf., Metallurgy Dept., University of Strathclyde, Glasgow, Jun. 1984, R1–R11.
Heiple, C. R. et al., "Mechanism for Minor Element Effect on GTA Fusion Zone Geometry," Welding J. 61, 97s, 1982.
Heiple, C. R. et al., "Effects of Minor Elements on GTAW Fusion Zone Shape," Trends in Welding Research in the U.S., (Ed. S. A. David) ASM, Metals Park, Ohio, 489–520, 1982.

*Primary Examiner*—Clifford C. Shaw
*Attorney, Agent, or Firm*—Donald R. Campbell; James C. Davis, Jr.; Paul R. Webb, II

[57] ABSTRACT

The weldability of a part formed from an alloy having low impurity concentrations is determined by initiating an arc between a stationary welding torch and the part using a predetermined set of welding parameters selected to produce a partially penetrating molten weld pool. The natural frequency of oscillation of the molten weld pool is measured a predetermined time following initiation of the arc, and the measured natural frequency of oscillation is compared to empirically determined data for the alloy to determine the weldability of the particular part. Variations in trace element concentrations between different heats of the same alloy affect the three-dimensional geometry of the molten weld pool, and in turn affect its resonant frequency. The invention may be used to adjust the welding parameters to accommodate differences in weldability between different heats of the same alloy.

18 Claims, 1 Drawing Sheet

METHOD OF DETERMINING THE WELDABILITY OF A PART

BACKGROUND OF THE INVENTION

This invention relates generally to arc welding processes, and more particularly to a method of determining the weldability of a part.

The aerospace industry, among others, frequently uses "super" or "exotic" alloys for fabricating parts and components, which entails a need to weld such materials. Such superalloys include nickel, cobalt and iron based alloys which have high strength at high temperatures. For example, Inconel 718 alloy is a nickel based superalloy. These alloys are typically characterized by rather low concentrations of trace elements or impurities such as sulfur or oxygen. The specifications for a particular alloy usually set maximum limits for impurity concentrations, and the concentrations of impurities can vary between different heats or casts of the same alloy. These cast-to-cast variations in impurity concentrations can cause different heats of the same alloy to exhibit substantially different weldability.

Within certain limits of trace element concentrations, the weldability characteristics of an alloy may not be appreciably affected. However, at low impurity concentrations, minor variations in concentrations of some trace elements can result in substantial variations in weld penetration. With certain alloys such as Inconel 718 alloy or Type 300 stainless steels, the impurity concentrations in the alloy, especially sulfur, determine its weldability. For sulfur concentrations above about 100-150 ppm (parts per million) variations in sulfur concentration have little affect on weldability. However, for sulfur concentrations below about 50-60 ppm, minor variations in concentration can result in substantial variations in weld penetration for the same welding parameters. Reduced penetration may result from too low a concentration, and differences in weld penetration may not be apparent to the human or machine welder as changes in the face side weld pool features are not readily discernable. This has caused problems in welding parts made from such alloys. The typical approach is to weld the parts and inspect them afterwards. The disadvantages of this approach are apparent. The parts may have to be discarded or the welded joint may have to be reworked in order to obtain the specified penetration. Chemical analysis of the parts prior to welding may have to be performed if problems have been repeatedly encountered.

It is desirable to provide a method of determining the weldability of a part prior to welding which avoids the foregoing difficulties by enabling appropriate changes in welding parameters to be made prior to welding so that a welded joint having the desired characteristics is obtained. It is to this end that the present invention is principally directed.

SUMMARY OF THE INVENTION

The invention affords a method of determining, by direct measurement, the weldability of a specimen or part formed of a given material, such as, for example, a superalloy or the like. The invention provides a rather simple and easily implemented measurement method which can be performed in real time on a real part just prior to welding using a rather simple sensor to determine the weldability of the part. This enables appropriate adjustments to be made to welding parameters if necessary to produce a welded joint having desired characteristics. The same sensor may also be used for the real time direct determination of weld pool penetration during welding.

As used herein with reference to one aspect of weldability, weldability refers to the depth-to-width (D/W) ratio of the weld bead, which is related to the three-dimensional geometry of the molten weld pool. High depth-to-width ratios are associated with a small heat-affected-zone (HAZ) and good weld penetration. Both good weld penetration and a small HAZ are desirable in gas-tungsten-arc (GTA) welding. The invention is based upon the recognition that the depth-to-width ratio of a welded joint is determined by the three-dimensional geometry of the molten weld pool, and that weldability may be assessed by measuring the natural, i.e., resonant frequency of oscillation of the molten weld pool since the natural frequency is related to the three-dimensional geometry. The three-dimensional geometry of the weld pool, and thus the natural frequency, depends, in turn, upon the material's surface tension which is affected by the trace element concentrations in the material. Surface tension affects the molten liquid flow dynamics in the weld pool and the related heat transfer processes, and thus affects the three-dimensional geometry of the weld pool.

Broadly stated, the invention affords a method of determining the weldability of a material which comprises initiating an arc between a stationary welding torch and a workpiece formed of the material using a predetermined set of welding parameters to produce a molten weld pool in the workpiece. The natural frequency of oscillation of the molten weld pool is measured at a predetermined time following initiation of the arc, and the measured natural frequency of oscillation is compared to empirically determined data for the material to determine the weldability of the workpiece.

In another aspect, the invention affords a method of determining the depth-to-width ratio of a weld pool in a part formed of an alloy in order to determine the weldability of the part comprising initiating an arc between a welding torch and the part using a predetermined set of welding parameters to produce a molten weld pool in the part; measuring the natural frequency of oscillation of the molten weld pool a predetermined time following initiation of the arc; and comparing the measured natural frequency of oscillation to a set of natural frequency values for different heats of the alloy, said natural frequency values being related to different depth-to-width ratios, in order to determine the weldability of the part.

Preferably, the welding parameters are selected to produce a partially penetrating weld pool in the workpiece, and the natural frequency is measured two to four seconds following initiation of the arc. By comparing the measured natural frequency to empirically determined data which relates natural frequency values to weldability for different heats of the same material, the weldability of the workpiece under test may be readily determined and, if necessary, appropriate adjustments to the welding parameters made so as to afford a welded joint having desired characteristics. The natural frequency of oscillation of the weld pool may be determined by exciting the weld pool at a plurality of different frequencies so as to produce spatial oscillations in the weld pool, sensing light reflected from the weld pool, then analyzing the sensed light to determine the natural frequency of oscillation. The sensor apparatus for determining natural frequency may be incorporated, at least partially, in the welding torch itself and used during actual welding to provide a continuous real time indication of the degree of penetration. A significant advantage of the method of the invention is that it may be incorporated into the welding process itself. This enables the weldability of an actual part to be determined by direct measurement on the part and enables the welding parameters to be tailored to the specific characteristics of the part.

Other advantages and features of the invention will become apparent from the description which follows.

DESCRIPTION OF THE PREFERRED EMBODIMENT

The method of the invention is particularly well adapted to determining the weldability of superalloys, such as Inconel 718 alloy and Type 300 stainless steels, and will be described in that context. As will become apparent, however, the invention is also applicable to other metals and alloys.

As previously indicated, it has been found that small variations in the concentrations of trace elements between different heats of certain materials such as low impurity alloys can have a profound effect on their weldability. The trace elements which appear to cause the greatest problem are those which act as surfactants, most notably sulfur, or those elements which combine with surfactants to inhibit their effect. It has been shown that at low concentrations variations in surfactant concentration cause variations in the surface tension versus temperature characteristics of the material, which in turn affects the weld pool liquid flow dynamics and the related heat transfer processes, and these produce variations in the three-dimensional geometry of the weld pool. FIGS. 1A-B and 2A-B are useful for illustrating these effects.

Figure 1A:
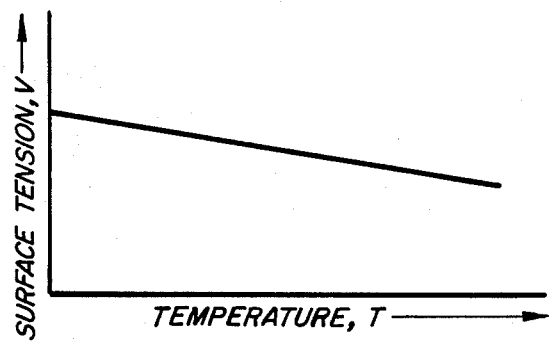
FIGS. 1A-B are, respectively, a curve illustrating an exemplary surface tension ($\gamma$) vs temperature (T) characteristic of a first heat of a particular base alloy and a cross sectional diagram illustrating a corresponding weld pool in a part formed of the alloy.
Figure 1B:
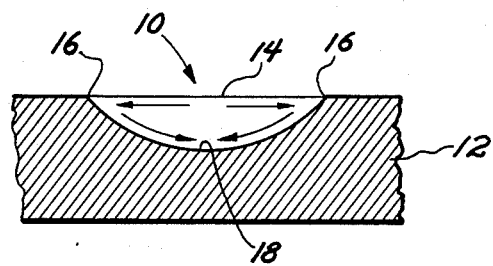
Figure 2A:
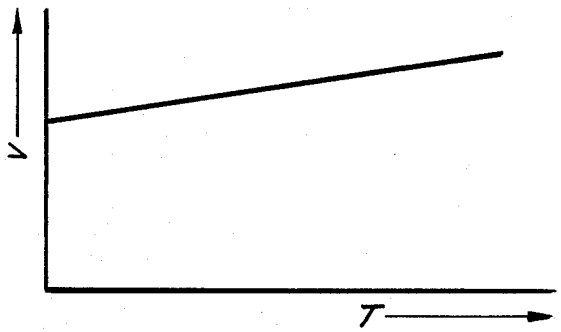
FIGS. 2A-B are similar to FIGS. 1A-B and illustrate the surface tension vs temperature characteristic of a different heat of the same base alloy and the corresponding cross section of the weld pool.
Figure 2B:
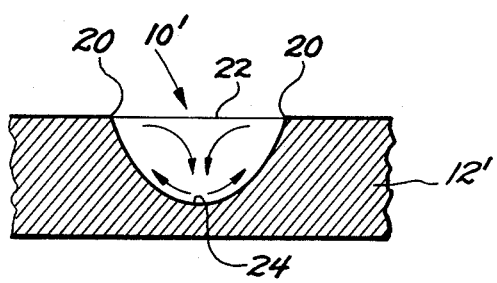

FIG. 1B is a cross sectional view showing the profile of a weld pool 10 produced by an assumed set of welding parameters in a low impurity alloy 12. FIG. 2B is a cross sectional view showing the profile of another weld pool 10' produced by the same welding parameters in another heat or cast 12' of the same alloy having different trace element concentrations. FIGS. 1A and 2A illustrate the corresponding surface tension ($\gamma$) vs temperature (T) characteristics of the two alloys. As shown in the figures, it has been found that the concentration of surface-active elements, such as sulfur, can affect the temperature dependence of surface tension ($d\gamma/dT$), and at low concentrations can change ($d\gamma/dT$) from a positive value to a negative value and consequently alter the direction of liquid metal flow in the weld pool. The flow in the pool is typically dominated by surface tension-driven-flow (Marangoni convection), the direction of which is from a region of low surface tension to one of high surface tension. FIGS. 1A-B are characteristic, for example, of a Type 300 stainless steel having a sulfur concentration of the order of 50 ppm or less, and FIGS. 2A-B are characteristic of the same stainless steel with a sulfur concentration of the order of 100 ppm. For sulfur concentrations above about 100-150 ppm, the surfactant saturates the surface of the material so that variations in its concentration do not substantially affect weldability.

As shown in FIG. 1A, where the concentration of surfactant is sufficiently low, the slope of the surface tension vs temperature characteristic will be negative. As noted above, liquids tend to flow from a region of low surface tension to one of high surface tension. Since the temperature at the center 14 of the surface of weld pool 10 will be higher than the temperature at the periphery 16 of the weld pool, the surface tension will be greater at the periphery and the molten liquid in the weld pool will flow from the center 14 (low surface tension region) to the edges 16 (high surface tension regions) of the weld pool, as indicated by the arrows in FIG. 1B. There will also be flow from edges 16 to the base 18 of the weld pool, as shown. Consequently, the heat carried by the liquid will cause further melting of the material at the edges of the pool, and a wide shallow pool will result. Conversely, when the surfactant concentration is sufficiently high to produce a surface tension vs temperature characteristic having a positive slope, as shown in FIG. 2A, the liquid metal will flow from the edges 20 of weld pool 10' (low surface tension regions) to the center 22 of the weld pool (high surface tension region), and also downwardly toward base 24 of the weld pool, as shown by the arrows in FIG. 2B. This inward and downward flow will cause further melting of the solid at the base 24 of the weld pool 10', producing a narrower deeper weld pool. The depth-to-width (D/W) ratio of weld pool 10' will thus be greater than the depth-to-width ratio of weld pool 10. High depth-to-width ratios are associated with a small heat-affected-zone (HAZ) and good weld penetration, which are desirable in gas-tungsten-arc welding. Accordingly, the material of FIG. 2B has better weldability than the material of FIG. 1B.

The figures illustrate that differences in weldability of a material are related to differences in the three-dimensional geometry of its weld pool. The invention measures a parameter which is related to the three-dimensional geometry and, thus, the depth-to-width ratio, of the weld pool to determine weldability. This parameter is preferably the natural frequency of oscillation of the weld pool, which the invention utilizes as a basis for determining weldability.

Externally exciting a molten weld pool will induce spatial oscillations in the weld pool. With proper excitation, the weld pool will oscillate at its natural or resonant frequency of oscillation. The natural frequency of a stationary weld pool is determined by its surface tension, its mass, and its three-dimensional geometry. The different geometries of weld pools 10 and 10' of FIGS. 1B and 2B, respectively, will produce different natural frequencies of oscillation.

In accordance with the invention, the natural frequencies of oscillation of samples of different heats of an alloy having known different trace element concentrations may be measured under specified conditions to develop empirical data for the alloy. The measured values of natural frequency may then be related to weldability by testing or inspection of the samples using conventional techniques. Depth-to-width ratios may be determined, for example, from measurements on cross sections of the samples through the weld bead. Subsequently, the weldability of a part formed of that alloy may be determined by measuring the natural frequency of oscillation of a weld pool produced in the part under the same specified conditions as those used to develop the empirical data, and comparing the measured natural frequency of oscillation to the empirically determined values. It is desirable that the weldability of a part be determined under the same conditions as those which would actually be used during welding. For example, some surface contaminants and oxides can cause penetration problems. If the surfaces of actual parts which are to be welded are first mechanically cleaned to remove surface oxides and other contaminants, this would also be done on a part being tested for weldability, as well as on the parts from which the empirical data is developed. In addition, the part being tested for weldability should have the same size and configuration as those used for developing the empirical data, and the fixturing and other conditions should similarly be the same.

A preferred manner of determining weldability in accordance with the invention is to first clean the part which is to be tested, if actual welding is to be done on a clean part and this is the manner in which the empirical data was developed. Otherwise, cleaning would not be done. An arc is then initiated between a stationary welding torch and the part using a predetermined set of welding parameters preferably selected to produce a partially penetrating molten weld pool in the part. The natural frequency of oscillation of the stationary weld pool is then measured (in a manner which will be described shortly) a predetermined time, e.g., 2-4 seconds, following initiation of the arc. Preferably, weldability is determined on an actual part as part of the welding process prior to the commencement of actual welding of the part. The measured natural frequency of oscillation of the weld pool is then compared against the empirical data to determine the weldability of the part. If the measured natural frequency is within acceptable limits, welding may commence. If the measured natural frequency is outside of the acceptable limits, welding may be aborted or the welding conditions modified to account for differences in the material. Modification of the welding conditions may involve changing the welding parameters as by increasing the power to obtain better penetration, or by taking actions to modify the constituents of the alloy to improve its weldability. The process of the invention may be performed automatically using a programmable welding apparatus, or it may be done under the manual control of an operator.

The natural frequency of oscillation of the molten weld pool may be measured in different ways. Preferably, it is done by exciting the weld pool at a plurality of different frequencies to induce spatial oscillations in the weld pool, sensing light reflected from the weld pool at a non-specular angle, and determining the excitation frequency which produces the greatest amount of reflected light. This excitation frequency corresponds to the natural frequency of oscillation of the weld pool. A method and an apparatus which may be employed by the invention for measuring the natural frequency of oscillation of the molten weld pool is disclosed in commonly assigned and allowed U.S. application Serial No. 934,522, filed Nov. 24, 1986, now U.S. Pat. No. 4,711,986, the disclosure of which is incorporated by reference herein.

The referenced application discloses a welding torch which incorporates a weld puddle, i.e., pool, and an imaging optical system comprising a lens mounted within the torch housing so as to view the molten weld pool at a non-specular reflection angle. The light received by the lens is focused onto the end of a fiber optics cable which transmits the received light to a light sensor. The light sensor measures the amount of light received and provides a corresponding electrical signal to a processor which analyzes the electrical signal to determine the natural frequency of oscillation. The weld pool may be excited to oscillation by modulating either the flow rate of a shielding gas which is supplied to the torch and which flows from the torch to the workpiece to envelop the arc, or by modulating the arc current. The modulation used to excite the weld pool may either be pulse modulation, which excites the pool simultaneously at a plurality of different frequencies, or a chirp, i.e., swept frequency. In the case of pulse modulation, the processor may perform a spectral analysis of the signal produced by the light sensor to detect the frequency component of the signal having the greatest amplitude. In the case of a swept frequency modulation, the processor may detect the time of occurrence within a swept frequency cycle at which the greatest signal occurs, and correlated this time to the corresponding frequency of the swept frequency modulator.

When the weld pool is in a non-perturbed or non-resonant condition, its surface is substantially flat and most of the light reflected from the weld pool surface is away from the puddle imaging optics which views the weld pool at a non-specular reflection angle. Accordingly, the output from the light sensor will be correspondingly low. When the weld pool is perturbed or excited, the molten material will undergo spatial oscillations and surface waves will temporally reflect light in a time-varying pattern, causing the output from the light sensor to vary in time in a similar manner. At resonance, the surface waves on the weld pool will cause the amount of light reflected to the puddle imaging optics to increase to a maxiumum value, thereby causing the signal from the light sensor to reach its maximum value. Thus, by correlating the excitation frequency to the peak of the signal from the light sensor, the natural frequency of oscillation may be determined readily.

The method and apparatus disclosed in the referenced application are intended to be used also during actual welding with a moving welding torch to detect full penetration of the part being welded. At full penetration, the resonant frequency of the molten weld pool abruptly decreases, and this decrease in natural frequency of oscillation may be used for controlling the welding process to produce full penetration. By employing the disclosed method and apparatus of the referenced application in the present invention to measure natural frequency of oscillation, the method of the invention may be conveniently incorporated into the welding process itself and performed prior to the commencement of actual welding to determine weldability. Thereafter, the same apparatus may be employed for monitoring weld penetration during the actual welding process. In some instances, it is desirable to have less than full penetration in a weld. Once the weldability of a particular part being welded has been determined, this information may be employed for adjusting the welding parameters to produce a desired degree of penetration, and the penetration monitored during actual welding by monitoring the resonant frequency of the weld pool. As noted above, this may be conveniently incorporated in an automatic control system for controlling the welding process.

Although a preferred embodiment of the invention has been shown and described, it will be apparent to those skilled in the art that changes can be made in this embodiment without departing from the principles and spirit of the invention, the scope of which is defined in the appended claims.

I claim:

1. A method of determining the weldability of a workpiece prior to a welding process by relating weldability to the three-dimensional geometry of a molten weld pool, comprising initiating an arc between a stationary welding torch and the workpiece using a predetermined set of welding parameters to produce the molten weld pool in the workpiece; measuring a natural frequency of oscillation of the molten weld pool a predetermined time following initiation of the arc; and comparing the measured natural frequency of oscillation to empirically determined data for the workpiece material to determine the weldability of said workpiece.

2. The method of claim 1, wherein said predetermined set of welding parameters is selected to produce partial penetration of the workpiece.

3. The method of claim 1, wherein said predetermined time is of the order of two to four seconds following arc initiation.

4. The method of claim 1, wherein said workpiece comprises an alloy having a low concentration of the order of 60 ppm or less of a trace element capable of producing variations in weldability of the alloy for small variations in concentration of the trace element.

5. The method of claim 4, wherein said trace element comprises sulfur.

6. The method of claim 1, wherein said measuring comprises exciting the weld pool at a plurality of different frequencies; sensing light reflected from the weld pool; producing a signal corresponding to the sensed light; and analyzing the signal to determine said natural frequency of oscillation.

7. The method of claim 6, wherein said exciting comprises modulating the flow rate of a shield gas supplied to the torch.

8. The method of claim 6, wherein the arc is formed by an electrical current flowing between an electrode of the welding torch and the workpiece, and said exciting comprises modulating said current.

9. The method of claim 6, wherein said exciting comprises exciting the weld pool using pulses, and said analyzing comprises performing a spectral analysis of said signal.

10. The method of claim 6, wherein said exciting comprises exciting the weld pool using a swept frequency, and said analyzing comprises measuring the time of occurrence of a peak of said signal and correlating said time to a frequency of said modulating.

11. The method of claim 6, wherein said sensing comprises sensing light reflected from the weld pool at a non-specular angle.

12. The method of claim 1 further comprising adjusting the welding parameters in response to said comparing to provide a preselected weld penetration.

13. The method of claim 1, wherein said method is performed as part of a welding process in which said workpiece is welded, and the method is performed prior to said welding of the workpiece.

14. The method of claim 1, wherein said empirical data is determined by measuring the natural frequencies of oscillation of different samples of the material of the workpiece using said predetermined set of welding parameters, and relating such natural frequencies of oscillation to weldability.

15. The method of claim 14, wherein said material comprises an alloy having low concentrations of trace elements, and said samples comprise different heats of said alloy with a range of weldabilities.

16. A method of determining the weldability of a part formed of an alloy from the depth-to-width ratio of a molten welding pool in the part, comprising initiating an arc between a welding torch and the part using a predetermined set of welding parameters to produce the molten weld pool in the part; measuring a natural frequency of oscillation of the molten weld pool a predetermined time after initiation of the arc; and comparing the measured natural frequency of oscillation to a set of natural frequency values for different heats of said alloy, which natural frequency values correspond to known depth-to-width ratios, to determine the weldability of said part.

17. The method of claim 16, wherein the welding torch is stationary and said predetermined set of welding parameters is selected to produce a partially penetrating weld pool in the part.

18. The method of claim 16, wherein the weldability of said part is determined prior to welding of the part, and the method further comprises adjusting the welding parameters based upon said comparing to afford a predetermined depth-to-width ratio.

* * * * *